United States Patent
Andrews et al.

(10) Patent No.: US 6,249,105 B1
(45) Date of Patent: Jun. 19, 2001

(54) SYSTEM AND METHOD FOR DETECTING PERFORMANCE COMPONENTS OF A BATTERY PACK

(76) Inventors: Neal Andrews, 1855 NW. 8th St.;
Gregory D. Brink, 1230 Clifton Ct.;
David L. Burton, 15150 NW. Orchard View Rd., all of McMinnville, OR (US) 97128

( * ) Notice: Subject to any disclaimer, the term of this patent is extended or adjusted under 35 U.S.C. 154(b) by 0 days.

(21) Appl. No.: 09/192,116

(22) Filed: Nov. 13, 1998

(51) Int. Cl.[7] .................................................... H02J 7/00
(52) U.S. Cl. ............................................................ 320/106
(58) Field of Search .................................. 320/106, 110, 320/112, 114, DIG. 12, DIG. 13; 307/125

(56) References Cited

U.S. PATENT DOCUMENTS

| | | | |
|---|---|---|---|
| D. 295,739 | 5/1988 | Lanci et al. | D13/5 |
| D. 372,456 | 8/1996 | Cooper et al. | D13/108 |
| D. 375,482 | 11/1996 | Andrews | D13/103 |
| 5,111,148 | 5/1992 | Senoo et al. | 324/433 |
| 5,183,714 | 2/1993 | Mitsui et al. | 429/123 |
| 5,200,686 | 4/1993 | Lee | 320/112 |
| 5,216,371 | 6/1993 | Nagai | 324/428 |
| 5,224,870 | 7/1993 | Weaver et al. | 439/157 |
| 5,227,262 | 7/1993 | Ozer | 429/98 |
| 5,248,927 | 9/1993 | Takei et al. | 320/113 |
| 5,350,317 | 9/1994 | Weaver et al. | 439/500 |
| 5,415,947 | 5/1995 | Mitsui et al. | 429/1 |
| 5,438,248 | 8/1995 | Hyuck | 320/106 |
| 5,470,343 | 11/1995 | Fincke et al. | 607/5 |
| 5,483,165 | 1/1996 | Cameron et al. | 324/427 |
| 5,510,205 | 4/1996 | Ozer | 429/91 |
| 5,573,870 | 11/1996 | Andrews | 429/96 |

(List continued on next page.)

*Primary Examiner*—Shawn Riley
*Assistant Examiner*—Pia Tibbits (57) ABSTRACT

A battery pack performance component detection system and method that identifies performance components of an installed battery pack which may be one of a number of battery packs each having a different performance component configuration. A performance component may be any operational component implemented in a battery pack other than the cells, that directly or indirectly affects the ability of a battery pack to support the power source requirements dictated by the operational mode of the battery-powered device. A performance component configuration is the particular combination of such performance components implemented in a battery pack. The battery packs have electrical and mechanical interfaces that are functionally interchangeable and include distinguishing feature(s) in either or both aspects of the battery interface that are uniquely associated with, and indicative of, the performance components implemented in the individual battery packs. The detection system includes one or more sensors appropriately configured and arranged to detect such distinguishing feature(s) and, based on the presence or absence of the feature(s), determines which performance components are implemented in the installed battery pack. The detection system may determine, for example, whether a battery pack installed in a battery-powered device is a commonly available industry standard battery pack having a first performance component configuration that is capable of supporting a first power source requirement, or a customized battery pack having a second performance component configuration capable of supporting a second power source requirement of the device. As used herein, an "industry standard" battery pack is any battery pack that generally is commonly available, whether it be due to a governmental regulation, industry-established standard, marketplace dominance or otherwise. In one application, the system determines whether battery pack installed in a portable defibrillator has a thermal fuse which limits the current draw, or a customized battery pack that does not.

19 Claims, 4 Drawing Sheets

U.S. PATENT DOCUMENTS

| | | | | |
|---|---|---|---|---|
| 5,575,807 | | 11/1996 | Faller | 607/5 |
| 5,602,454 | | 2/1997 | Arakawa et al. | 320/106 |
| 5,604,415 | * | 2/1997 | Vashi et al. | 320/106 |
| 5,608,306 | * | 3/1997 | Rybeck et al. | 320/106 |
| 5,625,291 | | 4/1997 | Brink et al. | 324/427 |
| 5,626,979 | | 5/1997 | Mitsui et al. | 429/97 |
| 5,627,449 | * | 5/1997 | Fujiki | 320/106 |
| 5,640,078 | | 6/1997 | Kou et al. | 320/124 |
| 5,646,501 | * | 7/1997 | Fishman et al. | 320/106 |
| 5,658,316 | | 8/1997 | Lamond et al. | 607/5 |
| 5,661,392 | * | 8/1997 | Imazaeki | 320/106 |
| 5,686,808 | * | 11/1997 | Lutz | 320/106 |
| 5,694,019 | | 12/1997 | Uchida et al. | 320/106 |
| 5,717,306 | * | 2/1998 | Shipp | 307/125 |
| 5,717,307 | * | 2/1998 | Barkat et al. | 307/125 |
| 5,721,482 | | 2/1998 | Benvegar et al. | 320/106 |
| 5,729,115 | | 3/1998 | Wakefield | 320/110 |
| 5,741,305 | | 4/1998 | Vincent et al. | 607/5 |
| 5,767,659 | * | 6/1998 | Farley | 320/106 |
| 5,780,992 | * | 7/1998 | Beard | 320/106 |
| 5,847,539 | * | 12/1998 | Akiya | 320/106 |
| 5,850,134 | * | 12/1998 | Oh et al. | 320/106 |
| 5,867,006 | * | 2/1999 | Dias et al. | 320/106 |
| 5,923,007 | * | 7/1999 | Emmert | 200/5 R |
| 5,927,483 | * | 7/1999 | Yamada | 200/343 |
| 5,959,371 | * | 9/1999 | Dooley | 307/130 |
| 6,014,008 | * | 1/2000 | Hartzell et al. | 320/106 |
| 6,014,009 | * | 1/2000 | Wierzbicki et al. | 320/106 |

* cited by examiner

SYSTEM AND METHOD FOR DETECTING PERFORMANCE COMPONENTS OF A BATTERY PACK

RELATED APPLICATIONS

This application is related to the following commonly owned applications filed concurrently herewith, some of which disclose subject matter disclosed in the present application.

U.S. Utility Patent Application Ser. No. 09/191,661 entitled "Battery Vibration Control Apparatus," filed concurrently herewith, and naming as inventors Cooper et al.; and U.S. Utility Patent Application Ser. No. 09/191,685 entitled "Battery Pack Chemistry Detection and Identification System and Method," filed concurrently herewith, and naming as inventors Andrews et al.

BACKGROUND OF THE INVENTION

1. Field of the Invention

The present invention relates generally to battery powered devices and, more particularly, to the detection and identification of performance components of a battery pack installed in such devices.

2. Related Art

Sudden cardiac arrest, i.e., a heart attack, has been attributed to over 350,000 deaths each year in the United States, making it one of the country's leading medical emergencies. Worldwide, sudden cardiac arrest has been attributed to a much larger number of deaths each year. One of the most common, and life threatening, consequences of a heart attack is the development a cardiac arrhythmia commonly referred to as ventricular fibrillation. When in ventricular fibrillation the heart muscle is unable to pump a sufficient volume of blood to the body and, more importantly, to the brain. Ventricular fibrillation is generally identifiable by the victim's immediate loss of pulse, loss of consciousness and a cessation of breathing. The lack of blood and oxygen to the brain may result in brain damage, paralysis or death to the victim.

The probability of surviving a heart attack or other serious heart arrhythmia depends on the speed with which effective medical treatment is provided. There are four critical components of effective medical treatment that must be administered to a victim of sudden cardiac arrest: (1) early cardiopulmonary resuscitation to keep the blood oxygenated and flowing to the victim's brain and other vital organs; (2) early access to emergency care; (3) early cardiac defibrillation to restore the heart's regular rhythm; and (4) early access to advanced medical care. If prompt cardiopulmonary resuscitation is followed by defibrillation within approximately four minutes of the onset of symptoms, the victim's chances of surviving sudden cardiac arrest can approach or exceed forty percent. Prompt administration of defibrillation within the first critical minutes is considered one of the most important components of emergency medical treatment for preventing death from sudden cardiac arrest.

Cardiac defibrillation is an electric shock that is used to arrest the chaotic cardiac contractions that occur during ventricular fibrillation and to restore a normal cardiac rhythm. To administer this electrical shock to the heart, defibrillator pads are placed on the victim's chest, and an electrical impulse of the proper size and shape is administered to the victim in the form of an electric shock. While defibrillators have been known for years, they have typically been large and expensive making them unsuitable for use outside of a hospital or medical facility.

More recently however, portable external defibrillators for use by first responders have been developed. A portable defibrillator allows proper medical care to be given to a victim earlier than preceding defibrillators, increasing the likelihood of survival. Such portable defibrillators may be brought to or stored in an accessible location at a business, home, aircraft or the like, ready for use by first responders. With recent advances in technology, even a minimally trained individual can operate conventional portable defibrillators to aid a heart attack victim in the critical first few minutes subsequent to onset of sudden cardiac arrest.

Portable defibrillators require a portable energy source to operate in the anticipated mobile environment. Several manufacturers have provided customized battery packs for their defibrillators. However, some portable defibrillators use a standard, commonly available, rechargeable battery pack, such as those used in video camcorders. Such battery packs are generally referred to herein as industry standard battery packs. The use of industry standard battery packs allows for a less expensive battery solution. These battery packs, while often having a standard mechanical and electrical interface, are available with different chemistries, such as lead acid, nickel cadmium, lithium or the like.

Certain battery-powered devices operate in accordance with certain modes of operation that place severe or otherwise specialized performance requirements on the power source. Such power source requirements must be supported by the installed battery pack for the device to operate in accordance with such operational modes when an alternating current power source is unavailable. However, industry standard battery packs are manufactured to support a wide range of battery-powered devices and, therefore, generally cannot support such specialized power source requirements. In addition to battery cells, battery packs include performance components that contribute to the ability of the battery pack to support such power source requirements. Performance components may be, for example, a thermal fuse, thermostat and current fuse.

Due to the inability of industry standard battery packs to meet a wide range of power source requirements, many device manufacturers also manufacture customized battery packs to support the specialized functions performed by the battery-powered device. Customized battery packs often have a performance component configuration that enables them to meet certain specialized power source requirements associated with certain devices or certain operational modes of a device.

Customized battery packs are, however, more expensive and less readily available than industry standard battery packs. As a result, rather than incurring the costs associated with the manufacture and use of such battery packs, many manufacturers limit the battery-powered device to those operations having associated power source requirements that can be adequately supported by industry standard battery packs. This, however, often results in the battery-powered device being configured to operate in modes which are not sufficient or at least not optimal for a given need of the device. In other words, the maximum performance of the battery-powered device is sacrificed for implementing a device that operates with industry standard battery packs.

An example of battery powered devices with specialized power source requirements are automatic external defibrillators (AEDs). Some of today's AEDs use industry standard camcorder sealed lead acid (SLA) battery packs such as the model LC-TA122P sealed lead acid battery pack available from Panasonic, Inc. AEDs require a large transfer of current in a short period of time when charging the energy delivery circuit. This places significant power source requirements on the installed battery pack. Such power source requirements generally cannot be satisfied by industry standard SLAs. As a result, rather than manufacturing customized battery packs that meet such specialized power source requirements, some AED manufacturers extend the time to charge the energy delivery circuit. There are drawbacks to this approach, however. Oftentimes, successful resuscitation of a defibrillating victim requires application of multiple defibrillation shocks. An increase in the time to charge the energy delivery circuit results in a corresponding increase in the time taken to deliver patient therapy.

What is needed, therefore is a technique for detecting performance components of battery packs. There is also a need for battery-powered devices that can modify the operational mode of the device based on the performance features that are provided in an installed battery pack.

SUMMARY OF THE INVENTION

The present invention is a battery pack performance component detection system and method that overcomes the above and other drawbacks of conventional battery pack techniques. Generally, the present invention identifies the performance components of an installed battery pack which may be one of a number of battery packs each having a different performance component configuration. A performance component includes any operational component implemented in a battery pack, other than the battery cells, that directly or indirectly affects the ability of a battery pack to support the power source requirements dictated by a battery-powered device or an operational mode of a battery-powered device. A performance component configuration is the particular combination of such performance components implemented in a battery pack.

The battery packs have electrical and mechanical interfaces that are functionally interchangeable. In addition, the battery packs include one or more distinguishing features in either or both aspects of the battery interface. The distinguishing features are uniquely associated with, and indicative of, the performance components implemented in the individual battery packs. The detection system includes one or more sensors appropriately configured and arranged to detect such distinguishing feature(s) on the battery interface. Based on the presence or absence of the distinguishing feature(s), the detection system determines which performance components are implemented in the installed battery pack.

In certain embodiments, a distinguishing feature identifies a performance component configuration while in other embodiments, each distinguishing feature identifies the presence or absence of a specific associated performance component. In such an embodiment, the detection of all such performance components is necessary to determine the performance component configuration of the battery pack.

In one particular embodiment, the present invention determines whether a battery pack installed in a battery-powered device is a commonly available industry standard battery pack having a first performance component configuration that is capable of supporting a first power source requirement, or a customized battery pack having a second performance component configuration capable of supporting a second power source requirement of the device. As used herein, an "industry standard" battery pack is any battery pack that generally is commonly available, whether it be due to a governmental regulation, industry-established standard, marketplace dominance or otherwise.

In addition to the first performance component configuration, the industry standard battery pack has standard mechanical and electrical battery interfaces. The standard mechanical interface enables the battery pack to mechanically interoperate with, and securely reside in, an appropriately configured battery pocket. Likewise, the standard electrical interface enables the battery pack to electrically interoperate with the battery pocket.

In addition to the second performance component configuration, the customized battery pack has a custom interface that includes the standard mechanical and electrical battery interfaces with the addition of one or more distinguishing features. The detection system detects the presence or absence of these distinguishing feature(s) and generates a performance component configuration indication accordingly.

One advantage of the present invention is that it enables a battery-powered device to be powered by battery packs in a cost effective manner by providing multiple custom battery packs that have interfaces interchangeable with an industry standard battery pack. The custom battery packs each have a particular performance component configuration that is different than the performance component configuration of the other customized battery packs as well as that of the industry standard battery pack. Selection may then be made of the battery pack that will perform optimally in the anticipated operating environment and, hence, most reliably supports the device during such operations.

When operating in accordance with one mode of operation that has power source requirements that can be satisfied by the performance component configuration of an industry standard battery pack, such a battery pack can then be used. When operating in accordance with another operational mode that places more demanding requirements on the power source, the customized battery pack that includes a performance component configuration that enables the customized battery pack to satisfy such power source requirements and having a battery interface operationally interchangeable with the industry standard battery pack can then be used.

The customized battery interface provides power in the same manner as the standard electrical interface while also including or eliminating detectable distinguishing features that identify the battery pack as being the customized rather than the industry standard battery pack. Thus, customized battery packs, which are commonly more expensive than industry standard battery packs, need only be used in those circumstances wherein the anticipated power source requirements dictate the use of such a battery pack or otherwise make the use of customized battery packs preferred. This may provide significant cost benefits to the extent that the industry standard battery is used. In such circumstances, commonly available and less expensive battery packs are used, reserving the relatively more expensive and less available customized battery packs for use only when necessary.

Further, the advantages associated with the selection of a battery pack capable of reliably supporting the anticipated operational mode of a battery-powered device cannot be overstated, particularly in medical devices such as portable defibrillators in which lack of such reliability can be life threatening.

Another advantage of the present invention is that it enables a device manufacturer to also manufacture multiple battery packs each having an operational configuration suitable for use in the device when operating in accordance with a particular mode of operation. Implementation of a performance component detection system and identification that distinguishes between industry standard and such custom battery packs facilitates incorporation of a battery pocket having a common design that mechanically and electrically interoperates with such industry standard battery packs. Customized battery packs having performance component configurations appropriate for specific modes of operation not supported by the industry standard battery pack may then be used with the same battery pocket. This significantly eliminates considerable development costs, resulting in a device that is economical to operate. Alternatively, a device manufacturer may design multiple battery packs with proprietary or uncommon mechanical and electrical interfaces. Although industry standard battery packs may not be used with devices designed to receive such customized battery packs, such proprietary or uncommon mechanical and electrical interfaces prevent other manufactures from producing, at least initially, replacement battery packs.

A still further advantage of the present invention is when the present invention is implemented in a battery-powered device that also implements a management system. In such devices, such as a portable defibrillator, the management system determines which operational modes of the device can be adequately supported by the installed battery pack. The management system configures the device to operate in accordance with a mode of operation that optimally utilizes the installed battery pack based on the performance component configuration of the installed battery pack. Other processes based on the performance component configuration of an installed battery pack can also be implemented. For example, if the manner in which the device is currently operated is contrary to the mode of operation for which the installed battery pack is best suited, indications of such an incompatibility between the performance component configuration and the current operational needs of the battery-powered device can be provided to the user.

A number of aspects of the invention are summarized below, along with different embodiments that may be included in each of the summarized aspects. It should be understood that the embodiments are not necessarily inclusive or exclusive of each other and may be combined in any manner that is non-conflicting and otherwise possible. It should also be understood that these aspects of the invention are exemplary only and are considered to be non-limiting.

In one aspect of the invention, a performance component detection system is disclosed. The detection system identifies a performance component configuration of an installed battery pack which may be one of a plurality of battery packs. As noted, a performance component configuration includes those operational components, if any, of the battery pack other than the cells that directly or indirectly affects the ability of the battery pack to support certain power source requirements dictated by the operational mode of the battery-powered device.

Each battery pack has a different performance component configuration and functionally interchangeable electrical and mechanical interfaces. The use of different performance component configurations enables the device to operate in accordance with different modes of operation, each placing a different requirement on the power source. The first performance component configuration enables the industry standard battery pack to support reliable and efficient device operations in accordance with a first operational mode while the second performance component configuration enables the customized battery pack to support reliable and efficient device operations in accordance with a second mode of operation.

Each battery pack also includes at least one distinguishing feature indicative of the performance components that comprises the performance component configuration of the battery pack. The distinguishing feature(s) is/are included in either the mechanical or electrical interface. The detection system includes one or more sensor devices constructed and arranged to detect the distinguishing feature(s) and a controller operationally coupled to the sensor that determines the performance component configuration based on a presence or absence of the distinguishing feature.

In another aspect of the invention a performance component detection system is disclosed. The system determines whether a battery pack installed in a battery-powered device battery pocket is a commonly available industry standard battery pack or a customized battery pack. The industry standard battery pack has one or more performance components forming a first performance component configuration and standard mechanical and electrical battery interfaces. The customized battery pack has one or more performance components forming a second performance component configuration that is different than the first performance component configuration and a custom interface. Along with the standard mechanical and electrical battery interfaces, the custom interface also includes one or more predetermined distinguishing features not otherwise provided by the standard battery interface. The distinguishing feature(s) are indicative of the different performance component configuration implemented in the customized and industry standard battery packs.

The detection system is constructed and arranged to detect a presence or absence of such distinguishing feature(s) and to generate, based on the results of this detection, one or more signals indicating whether the installed battery pack has the first or the second performance component configuration. Specifically, in one embodiment, the detection system includes a sensing device constructed and arranged to detect a presence or absence of each distinguishing feature(s) and a signal generating circuit electrically connected to the sensing device for generating the battery pack performance component configuration identification signal.

The distinguishing feature may, as noted, reside on the mechanical or electrical interface of the battery packs. In one embodiment, the distinguishing feature(s) include a recess on the customized battery pack and the sensing device is a switch. The recess has a dimension suitable for receiving an actuator of the switch so as not to activate the switch when the customized battery pack is installed within the battery pocket. The industry standard battery pack lacks such a recess and, as such, activates the switch when the industry standard battery pack is installed in the battery pocket. In one preferred embodiment, the sensing device is a tact switch with a spherical actuator and the corresponding recess is similarly spherical in shape. This reduces the adverse effect such a recess has on the strength of the battery pack wall. It should be noted that the depression may be located on any part of the battery pack interface surface that does not interfere with the mechanical and electrical interface of the battery pack, while the switch is located in a corresponding location in the battery pocket interface to mate with the recess. The presence and absence of the distinguishing feature(s) is not significantly great to be considered an operational difference in the mechanical or electrical interface provided by the two battery packs, yet it is sufficiently different to be detectable.

In an alternative embodiment, the distinguishing features may include features detectable by other means, such as a reflective or colored strip secured to the battery pack interface surface and the like. In all such alternative embodiments, the sensing device includes an appropriately located electrical contact, optical sensor or the like appropriately disposed within the battery pocket to sense the presence and absences of the distinguishing feature.

In a still further aspect of the invention, a battery-powered device such as a portable defibrillator is disclosed. The device has a plurality of operational modes each having associated therewith a characteristic power source requirement. The device includes a battery pocket constructed and arranged to receive and operate with an industry standard battery pack. The industry standard battery pack has a first performance component configuration and standard mechanical and electrical battery interfaces. A customized battery pack having a second performance component configuration different than the first performance component configuration is also available for use in the same battery pocket. The customized battery pack has a custom interface that includes the standard mechanical and electrical battery interfaces, as well as one or more distinguishing features indicative of the second performance component configuration and not provided on the battery interface of the industry standard battery pack. and indicative of the second performance component configuration. The distinguishing feature may be located on the standard mechanical interface or standard electrical interface of the customized battery pack.

The device also includes a performance component configuration detection and identification system constructed and arranged to detect a presence or absence of such distinguishing features. The system generates a performance component configuration identification signal indicative of the performance component configuration of a battery pack installed in the battery pocket. In one embodiment, the system includes a sensing device constructed and arranged to detect a presence or absence of the distinguishing feature (s). It also includes an identification unit operationally coupled to the sensing device for generating the configuration identification signal based on the presence or absence of the distinguishing feature(s).

The industry standard battery packs oftentimes have a thermal fuse as one operational component to limit the discharge current of the battery. This enables the industry standard battery pack to support reliable and efficient device operations in accordance with a first operational mode wherein the device is operated in a manner that does not require a discharge current beyond the capabilities of the industry standard battery pack. The customized battery pack may include different performance components forming the second performance component configuration.

In one embodiment, the customized battery pack is capable of supporting power source requirements such as a high discharge current. In such an embodiment, the performance component configuration of the customized battery pack includes the lack of a thermal fuse; that is, the performance component configuration of the customized battery pack includes no performance components. In such an embodiment, the customized battery pack supports reliable and efficient device operations in accordance with a second operational mode.

In a still further aspect of the invention, a customized battery pack is disclosed. The customized battery pack includes a mechanical and an electrical interface substantially the same as that provided by an industry standard battery pack, along with a performance component configuration that is different than a performance component configuration provided in the industry standard battery pack. The customized battery pack also includes one or more distinguishing features indicative of the different performance component configuration located on either of the mechanical and electrical interfaces that is not provided on the industry standard battery interface. In one embodiment, the performance component configuration of the industry standard battery pack includes a thermal fuse while the performance component configuration of the custom battery pack does not include a thermal fuse.

As noted above, the present invention provides numerous advantages. Various embodiments of the present invention provide certain advantages and overcome certain drawbacks of conventional techniques while other embodiments provide the same or different advantages and overcome the same or other drawbacks in the same or different manner. Thus, not all embodiments of the invention share the same advantages and those that do may not share them under all circumstances. Further features and advantages of the present invention as well as the structure and operation of various embodiments of the present invention are described in detail below with reference to the accompanying drawings.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps, in which the left-most one or two numerals of a reference numeral indicate the number of the figure in which the referenced element first appears, and in which.

DETAILED DESCRIPTION

The present invention is a battery pack performance component detection system and method that overcomes the above and other drawbacks of conventional battery pack techniques. Generally, the present invention identifies the performance components of an installed battery pack which may be one of a number of battery packs each having a different performance component configuration. A performance component includes any operational component implemented in a battery pack, other than the battery cells, that affects the ability of a battery pack to support power source requirements dictated by the operational mode of the battery-powered device.

The battery packs have electrical and mechanical interfaces that are functionally interchangeable. In addition, the battery packs include one or more distinguishing features in either or both aspects of the battery interface. The distinguishing features are uniquely associated with, and indicative of, the performance components implemented in the individual battery packs. The detection system includes one or more sensors appropriately constructed and arranged to detect such distinguishing feature(s) on the battery interface. Based on the presence or absence of the distinguishing feature(s), the detection system determines which performance components are implemented in the installed battery pack, and hence, the performance component configuration of the installed battery pack.

Figure 1:
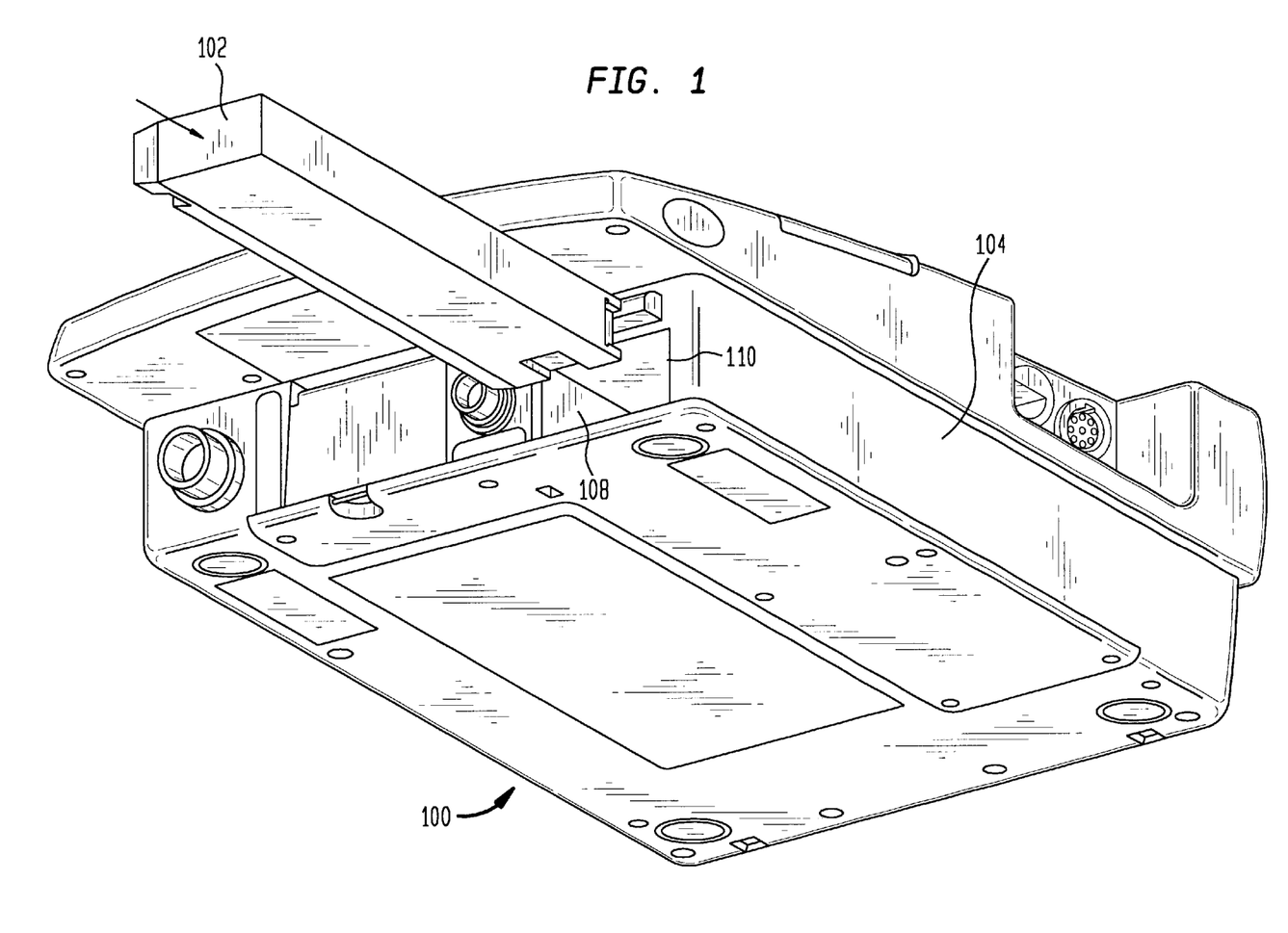
FIG. 1 is a perspective view of a defibrillator suitable for implementing one embodiment of the performance component detection and identification system of the present invention.

The present invention may be implemented in virtually any battery-powered device. However, the illustrated embodiments of the present invention are shown particularly in connection with a battery-powered defibrillator. FIG. 1 is a perspective view of one such defibrillator suitable for implementing one embodiment of the battery performance component detection and identification system of the present invention. Portable defibrillator 100 may be, for instance, model M3500B automatic external defibrillator (AED) available from the Hewlett-Packard Company, Andover, Mass., USA.

In accordance with the present invention, defibrillator 100 may be operated in accordance with different "modes of operation." As used herein, the terms "modes of operation" and "operational modes" are defined primarily by power usage requirements placed on an installed battery pack by the device. For example, in one embodiment of the exemplary application of defibrillator 100, operational modes are primarily defined by battery current discharge quantity and time.

The installed battery pack 102 has a number of operational features that enable it to support the power source requirements placed on the battery pack by the different operational modes of the device. Of particular concern to the present invention is the presence or absence in the installed battery pack 102 of performance component or components that impact this capability of the battery pack. A performance component configuration, then, of an installed battery pack comprises those performance components, if any, that are included in the battery pack in addition to the battery cells.

A replaceable battery pack 102 is electrically and mechanically mounted in a battery pocket 104 of defibrillator 100. As is common with many devices which utilize battery packs, battery pocket 104 includes a sleeve 108 terminating in an opening 110 through which battery pack 102 is inserted into sleeve 108.

Battery pocket 104 is configured to electrically and mechanically interface with battery packs having a predefined electrical ad mechanical interface. In the illustrative embodiment, defibrillator battery pocket 104 is configured to electrically and mechanically interface with an industry standard battery pack. An industry standard battery pack is one that is commonly available and, as a result, is readily available and often low in cost. The industry standard battery pack has a performance component configuration (discussed below) and standard mechanical and electrical battery interfaces. For example, in the illustrative embodiment, the defibrillator 100 is configured with a battery pocket 108 adapted to mechanically and electrically interface with a Panasonic LCS-23 12P sealed lead acid (SLA) battery pack commonly used in video camcorders and other consumer electronic devices.

As noted, it is preferable that the battery pack 102 installed in defibrillator 100 is that which is best suited for the anticipated power source requirements placed on the installed battery pack by the device when operating in accordance with an anticipated mode of operation. To accommodate different modes of operation of defibrillator 100, or different defibrillators 100 each operating in accordance with a single, different operational mode, customized battery packs are provided. The customized battery packs have different performance component configurations and, in accordance with the present invention, a custom interface. To be used with defibrillator 100, the custom battery pack has functionally interchangeable electrical and mechanical interfaces with the industry standard battery pack and a different performance component configuration.

One use of the present invention is to select a battery pack that is appropriate for the anticipated operational mode of defibrillator 100. In one preferred embodiment, however, the reverse is implemented. That is, the operational mode implemented in defibrillator 100 is determined by the performance component configuration of battery pack 102 currently installed in battery pocket 104. It is this latter embodiment that is described below.

As noted, of particular concern to the present application is the presence or absence of performance components. To determine the performance component configuration implemented in the battery pack 102 currently installed in battery pocket 104, the custom interface on the customized battery pack includes, in addition to the standard mechanical and electrical battery interface implemented in the industry standard battery pack, one or more distinguishing features. In accordance with the present invention, the distinguishing feature(s) are indicative of the different performance component configurations implemented in the custom and industry standard battery packs.

Importantly, these distinguishing features are predetermined detectible differences that may be located at one or more locations on the battery interface and which do not interfere with the interchangeability of the electrical and mechanical interfaces of the customized and industry standard battery packs. It should become apparent from the following description that such features may be the presence or absence of any feature on either the industry standard or customized battery pack. The following description addresses two battery packs, an industry standard battery packs and one customized battery pack, for which only one distinguishing performance component, a thermal fuse, is required to distinguish therebetween. It should be understood, however, that any number of customized battery packs necessary to support different operational modes of defibrillator 100 may be implemented. Furthermore, additional performance components may form the performance component configuration of either or both the industry standard and customized battery pack. In such embodiments, individual distinguishing features associated with each of the performance components may be included, with the sum of such distinguishing features determining the performance component configuration of the installed battery pack 102.

Figure 2:
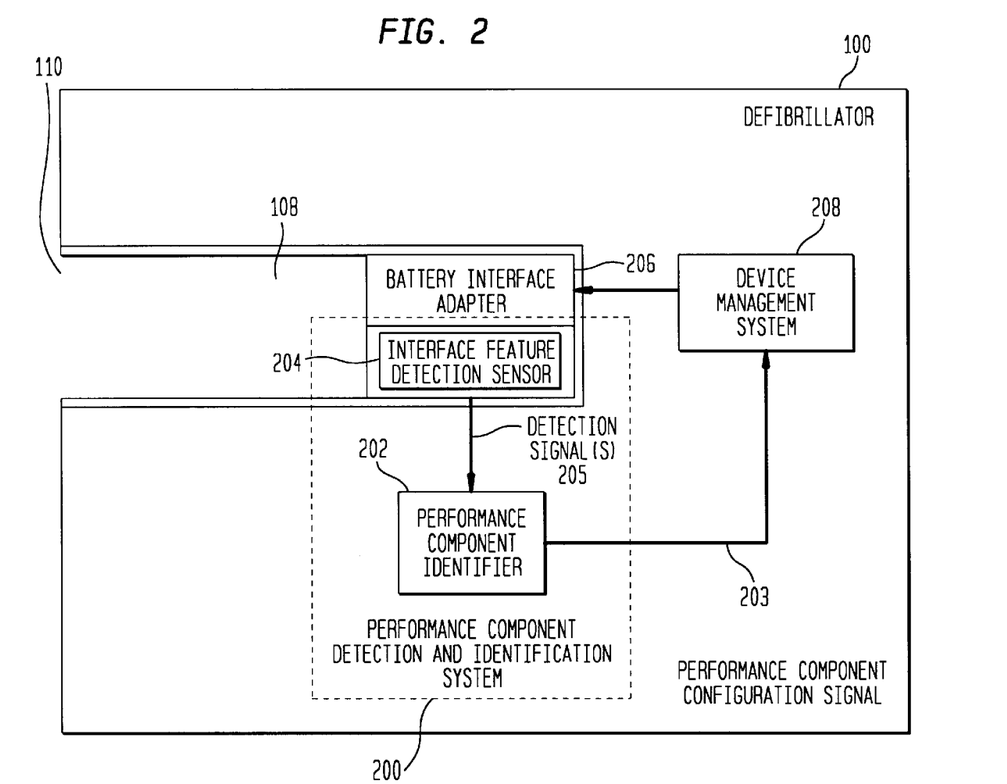
FIG. 2 is a schematic block diagram of the defibrillator shown in FIG. 1 illustrating the battery performance component detection and identification system.

FIG. 2 is a block diagram of one embodiment of the battery performance component detection and identification system implemented in defibrillator 100. Battery performance component detection and identification system 200

("system 200") primarily includes an interface feature detection sensor 204 and a battery performance component configuration identifier 202. Interface feature detection sensor 204, or simply sensor 204, is constructed and arranged to detect the one or more distinguishing features on the battery pack interfaces of the customized and industry standard battery packs. Sensor 204 generates one or more detection signals 205 indicating which distinguishing feature or features have been detected on the installed battery pack 102. The battery performance component identifier 202 determines the performance component configuration of the installed battery pack 102 based on a presence or absence of the distinguishing features as set forth in the detection signal(s) 205. Identifier 202 generates a performance component configuration signal 203 indicating such for use by other systems of defibrillator 100. It should be appreciated that if many customized battery packs, each with a different performance component configuration, are provided, then more than one distinguishing feature may be used to uniquely identify the presence or absence of each performance component of each battery pack. A corresponding increase in detection signals 205 and performance component configuration indicator signals 203 may then be implemented.

As noted, this description addresses one particular application of the present invention in a defibrillator that can operate in accordance with multiple modes of operation. In this particular embodiment, defibrillator 100 also includes a device management system 208 that determines which operational mode that defibrillator 100 will operate based on the performance component configuration of the installed battery pack 102. That is, defibrillator 100 automatically reconfigures certain systems to optimally draw power from and otherwise maintain installed battery pack 102, as well as to operate most reliably given the performance component configuration of the installed battery pack 102. Manual selection by the operator is implemented in alternative embodiments.

As shown in FIG. 2, a battery interface adapter 206 is located at an end of battery pocket 104 to electrically and mechanically interface with a battery pack 102 installed in sleeve 108. As will be described in further detail below, in the illustrative embodiment, sensor 204 is mounted in battery interface adapter 206. In one embodiment described below, battery interface adapter 206 includes a printed circuit board (PCB) on which performance component configuration identifier 202 is implemented. In such embodiments, then, the entire system 200 is implemented within battery interface adapter 206. Alternatively, detection sensor 204 could be appropriately configured to generate sufficiently strong detection signals 205 to be received by a remotely located battery performance component identifier 202.

It should also be understood that any means for communicating between sensor 204 and identifier 202, as well as between system 200 and other components of defibrillator 100 may be used. This may include, for example, dedicated communication lines, data buses, shared memory, or the like. The selection of such techniques and systems are considered to be well known design selections not pertinent to the present invention.

One exemplary implementation of the present invention will now be described with reference to FIGS. 3–5. This implementation is provided to enable defibrillator 100 to operate in accordance to two modes of operation. In a first operational mode defibrillator 100 has associated therewith a power source requirement in which the installed battery pack 102 must be capable of supporting the discharge of a significant quantity of current over a short time period, on the order of 11 amperes over 3 seconds. In a second operational mode, the defibrillator 100 has associated with in a less stringent power source requirement in which the installed battery pack must be capable of supporting the discharge of 0.5 amperes over 2.5 hours.

As noted, defibrillator 100 is configured to operate with industry standard battery packs, such as the model LCS-2312P sealed lead acid battery pack available from Panasonic, Inc. Such industry standard battery packs include a thermal fuse. The thermal fuse affects the ability of the industry standard battery pack to support power source requirements. As such, the thermal fuse is considered to be a performance component in accordance with the present invention. The industry standard battery pack has a performance component configuration, then, of a single performance component.

The current discharge requirement established by the first mode of operation causes the temperature of the industry standard battery pack to increase, eventually surpassing the threshold of the thermal fuse, causing the battery pack to become unavailable. Such an occurrence is not experienced when the defibrillator 100 is operated in accordance with the second mode of operation. That is, the industry standard battery pack can support the power source requirements associated with the second mode of operation.

To support the power source requirements associated with the first mode of operation, a single customized battery pack that does not contain the thermal fuse is provided in this illustrative example. Such a battery pack can withstand greater temperatures. As such, a greater current draw as required by the first operational mode can be supported by the customized battery pack.

Thus, in this example, there are two battery packs: an industry standard battery pack that supports the second power source requirements dictated by the second mode of operation, and a customized bakery pack that supports the first (and second) power source requirements as set forth by the defibrillator 100 operating in accordance with the first (and second) mode of operation. The industry standard battery pack has a first performance component configuration comprising a single performance component: the thermal fuse. The customized battery pack has a second performance component configuration that comprises no performance components. In this exemplary application of the present invention, the management system 208 interoperates with the defibrillator to allow the use of the industry standard battery pack for high current draw applications by slowing down the current draw so as to not actuate the thermal fuse.

Figure 3:
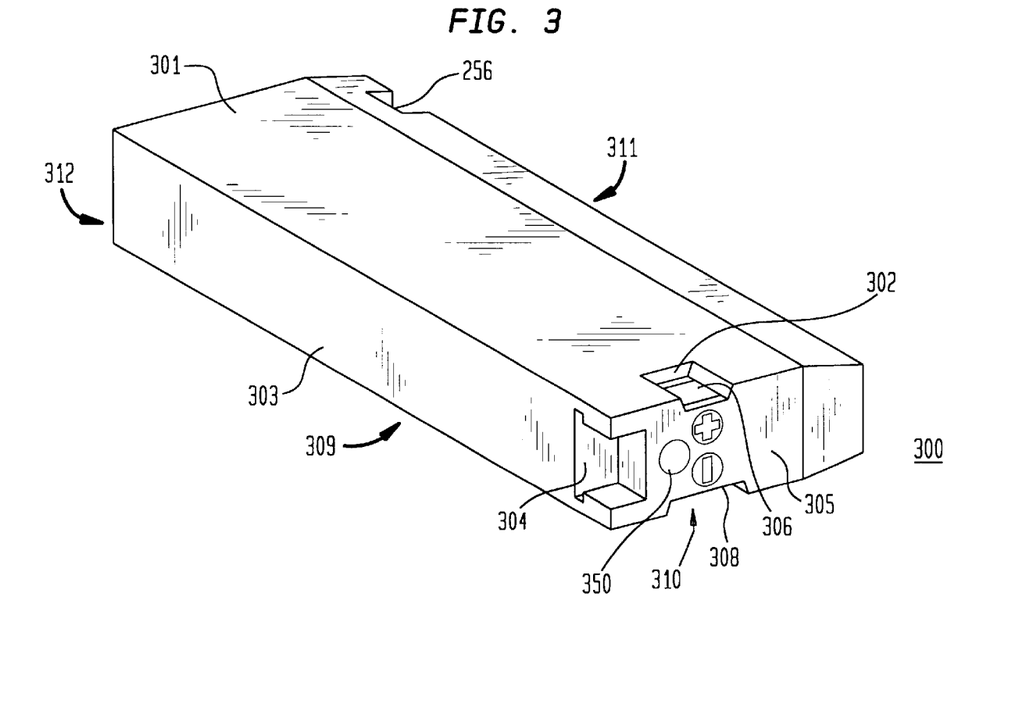
FIG. 3 is a perspective view of an exemplary customized standard battery pack implemented in accordance with one embodiment of the present invention to include a single distinguishing feature on the battery pack interface.

FIG. 3 is a perspective view of customized battery pack 300 configured in accordance with one embodiment of the present invention suitable for use in battery pocket 104 illustrated in FIG. 1. Battery pack 300 has electrical and mechanical interfaces that mate with corresponding interfaces on battery interface adapter 206 in battery pocket 104. Battery pack 300 is an elongate battery pack having four elongate sides, two of which, 301, 303, are shown in the perspective view of FIG. 3. In the orientation shown in FIG. 3, side 301 is referred to as top side 301 and side 303 is referred to as right side 303. It follows then that the side opposite top side 301 (not shown) is referred to herein as the bottom side 309 while the side opposite right side 303 (also not shown) is referred to as left side 311. A front end side 305 at the front end of battery pack 300 mates with battery interface adapter 206 when battery pack 300 is installed in battery pocket 104. A rear end side 312 (not shown) is exposed to the operator when installed in defibrillator 100.

In the illustrative embodiment, electrical and mechanical interfaces of battery pack 300 include a number of recesses on its side surfaces. Certain recesses have disposed therein battery terminals while others do not. Specifically, a recess 302 formed in the surfaces of top side 301 and front end side 305 houses positive terminal 306 while a recess 310 formed in the surfaces of bottom side 309 and front end side 305 houses negative terminal 308. In accordance with one embodiment of the present invention, and as will be described in detail below, a recess 304 is also formed in the surface of right side 303 and front end side 305. As should be apparent, recesses formed in front end side 305 and another side 301,303,309 can mate with properly aligned and dimensioned protrusions extending into sleeve 108 of battery pocket 104. In this illustrative embodiment, such protrusions reside on battery interface adapter 206 which, as noted, is mounted within battery pocket 104.

In accordance with one embodiment of the present invention, front end side 305 has formed therein a recess 350 adapted to receive an actuator of a switch mounted on battery interface adapter 206 described below. The recess 350 identifies this battery pack as comprising a particular performance component configuration. In one specific embodiment, this recess 350 distinguishes the customized battery pack 300 from an industry standard battery pack having the same mechanical and electrical interfaces. The industry standard battery pack, a Panasonic Model LCS-2312P, does not have such a recess at the same location on the front end side 305.

Figure 4:
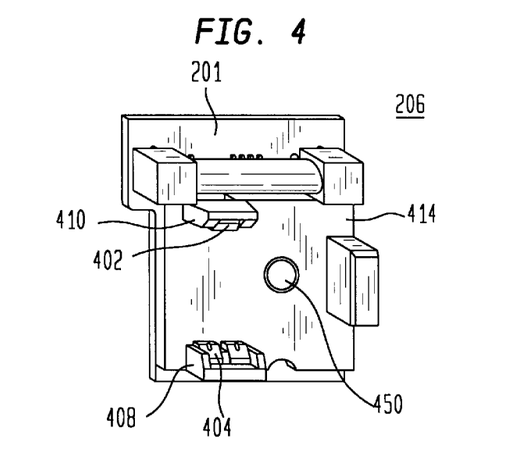
FIG. 4 is a perspective view of one embodiment of a battery interface adapter, suitable for mounting in the battery pocket shown in FIG. 1, incorporating the battery performance component detection sensor of one embodiment of the present invention.

FIG. 4 is a perspective view of one embodiment of the battery interface adapter 206 mounted in battery pocket 104. Battery interface adapter 206 includes protrusions 408, 410, 412 extending from a base 201 into battery pocket 104. In the illustrative embodiment, base 201 is a printed circuit board. These protrusions, also commonly referred to as extensions, arms and the like, are aligned with recesses 302, 304 and 310, and are dimensioned to mate with the corresponding recess when battery pack 102 is installed in battery pocket 104. As used herein, a recess and corresponding protrusion are dimensioned such that the protrusion easily slides into the corresponding recess as battery pack 102 is installed in battery pocket 104.

In the illustrative embodiment, battery interface adaptor 206 includes a positive contact 402 constructed and arranged to electrically mate with the positive terminal 306 of the installed battery pack 102. Likewise, battery interface adaptor 206 includes a negative contact 404 constructed and arranged to mate with the negative terminal 308 of the installed standard battery pack.

In accordance with the present invention, sensor 204 is implemented as a switch 450 on battery interface adaptor 206. This switch 450 detects the presence or absence of the recess 350 on an installed battery pack 102. To perform such a detection, the switch is positioned to be longitudinally aligned with the recess 350. In this embodiment, the detection signal 205 generated by detection sensor 204 is nothing more than either an open circuit or a ground signal. As noted, this detection signal 205 is provided to battery performance component identifier 202. In certain embodiments, the detection signal 205 is amplified, filtered or otherwise conditioned prior to being generated.

Figure 5:
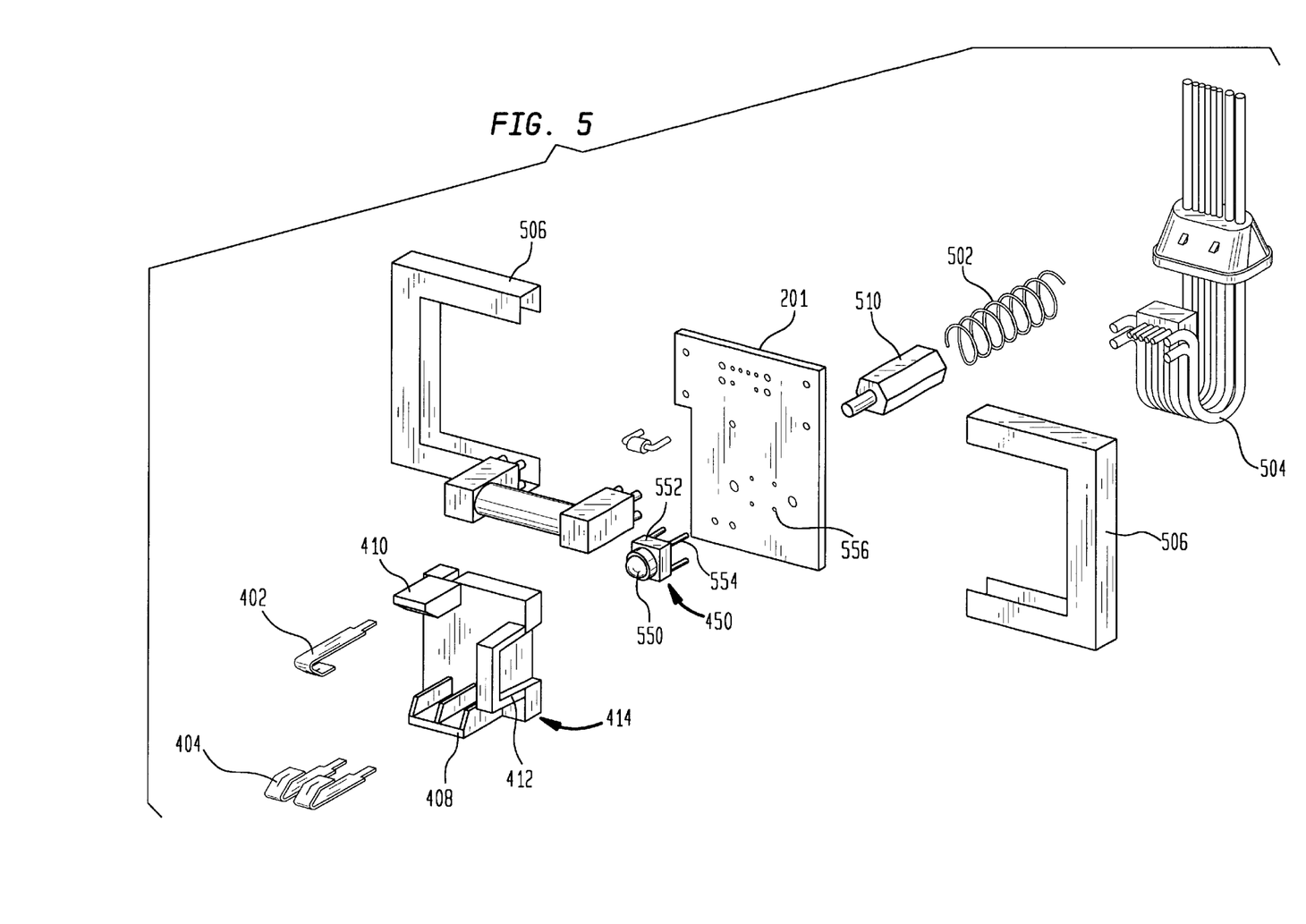
FIG. 5 is an exploded perspective view of one embodiment of the battery interface adapter illustrated in FIG. 4.

FIG. 5 is an exploded perspective view of one embodiment of the battery interface adapter illustrated in FIG. 4.

Base 201 is preferably a printed circuit board (PCB) that is electrically connected to contacts 402 and 404, and switch 450, as well as other components of battery interface adapter 206 not relevant to the present invention. Contacts 402, 404 are mounted in channels formed in a side of protrusions 408, 410 facing battery terminals 306, 308, and have extension arms which extend through the unitary assembly 414 to be mechanically and electrically secured to printed circuit board 201. A spring 502 is mounted on a stand off member 510 mounted to the rear face of printed circuit board 201. Spring 502 is compressed against a stationary reference surface (not shown) and the rear surface of base 201, providing a predetermined force against base 201. Pairs of opposing tracks 506 are positioned at the rear of battery pocket 104 a sufficient distance apart from each other to loosely restrain the printed circuit board 201. An electrical cable 504 is attached to printed circuit board 201 for transferring current, data, etc. from adapter 206 to other defibrillator components. These and other features of battery interface adapter 206 and battery pack 102 are described in commonly owned U.S. Utility Patent Application entitled "Battery Pack Chemistry Detection and Identification System and Method," filed concurrently herewith under Ser. No. 09/191,685 and naming as inventors Andrews et al.; and commonly owned U.S. Utility Patent Application entitled "Battery Vibration Control Apparatus," filed concurrently herewith under Ser. No. 09/191,661, and naming as inventors Cooper et al., the disclosures of which are hereby incorporated by reference in their entirety.

In accordance with one embodiment of the present invention, printed circuit board 201 has mounted thereon switch 450. Switch 450 has leads 554 mounted in receiving holes 556 in PCB 201, in which the leads 554 are electrically connected to traces in a well known manner. Switch 450 includes an actuator 550 mounted on a base 552 that includes a electrical switch (not shown) that receives and generates a signal through certain pins 554.

In embodiments wherein the identifier 202 is included on PCB 201, then cables 504 are used to transfer performance component configuration signal 203 to management system 208. On the other hand, in embodiments in which identifier 202 is remotely located, cables 504 are used to transfer detection signals 205.

As best shown in FIG. 4, the actuator 550 extends through a channel (not shown) in unitary assembly base 414 into battery sleeve 108. When the customized battery pack 300 is installed in the battery pocket 104, the switch 450 is not actuated as recess 350 prevents contact between the front end face 305 of customized battery pack 300 and the actuator 550. On the other hand, no such recess exists on the industry standard battery pack. The front face of the industry standard battery pack contacts the actuator 550, causing it to travel the requisite distance to activate switch 450.

In one embodiment, switch 450 is a tact switch. In one preferred embodiment, switch 450 is a long travel momentary tact switch having a spherical actuator such as the model KSJOM431 switch available from ITT Cannon, Eden Prairie, Minn., USA. In this embodiment, corresponding recess 350 is similarly spherical in shape. This reduces the adverse effect such a recess 350 has on the strength of the battery pack wall.

It should be noted that the recess 350 may be located on any part of the battery pack interface surface 305 that does not interfere with the mechanical and electrical interface of the battery pack, while the switch is located in a corresponding location in the battery pocket interface to mate with the recess.

Having now described various embodiments of the invention, it should be apparent to those skilled in the relevant art that the foregoing are illustrative and not limiting, having been presented by way of example only. For example, it should be understood that in alternative embodiments of the present invention, distinguishing features and detection sensors may be configured to use other mediums for communicating different battery chemistries. For example, in one alternative embodiment, the distinguishing features may include a reflective coating or label placed on front end side 305 of customized battery pack 300. An appropriately aligned photo detector is provided as sensor 204 to detect the presence or absence of such a distinguishing feature. In still alternative embodiments, other mechanisms such as magnetic may be used. In still further embodiments, a communication port may be provided on front face 305 of customized battery pack 300 through which a circuit located in customized battery pack 300 communicates an identification of the performance components in the battery pack. In such an embodiment, sensor 204 would include a receiver that receives and interprets such signals. As one skilled in the art should find apparent, any means for communicating the performance components of the installed battery packs may be used in accordance with the present invention. Also, in the illustrative embodiment, battery pack 102 is a Panasonic battery model LCS-2312P battery pack commonly used in video camcorders and other consumer electronic devices. It should also be understood that other battery packs such as Panasonic battery model nos. LCT1812P, LCT-1912AP, and LCS-2012P may be used. In such embodiments, other configurations of the present invention would be implemented to support such alternative battery packs. Further, non-standard or specialty battery packs may also be used. Numerous other embodiments and modifications thereof are contemplated as falling within the scope of the present invention as defined by appended claims and equivalents thereto.

What is claimed is:

1. A battery identification system that identifies performance components of one of a plurality of battery packs, each having functionally interchangeable electrical and physical interfaces and a distinguishing feature indicative of at least one implemented performance component, the system comprising:

a sensor device constructed and arranged to detect said distinguishing feature; and a controller operationally coupled to said sensor that determines a battery performance configuration based on a presence or absence of said distinguishing feature, wherein said performance configuration comprises a combination of one or more performance components, other than the battery cells themselves, that directly or indirectly affects the ability of a battery pack to support the power source requirements dictated by an operational mode of a battery powered device to which the battery pack is connected, said controller outputting a signal that enables the adjusting of the operation of the device based on the battery performance configuration.

2. A battery performance component identification system, disposed within a battery pocket of a battery-powered device operational in accordance with a plurality of operational modes, based on a said installed battery pack selected from a commonly available industry standard battery pack or a customized battery pack, the industry standard battery pack having a first performance component configuration and a standard battery interface including a standard mechanical and a standard electrical battery interface, said customized battery pack having a second performance component configuration different than said first performance component including a set of performance components, other than the battery cells, that directly or indirectly affects the ability of the customized battery pack to support the power source requirements dictated by an operational mode of a battery powered device to which the customized battery pack is connected and a custom interface comprising said standard mechanical battery interface, said standard electrical battery interface and one or more distinguishing features not found in said standard battery interface, said battery performance component identification system comprising:

identification circuitry constructed and arranged to detect a presence or absence of said one or more distinguishing features and for generating a battery pack performance component configuration identification signal identifying whether said installed battery pack has said first or said second performance component configuration; and operational circuitry that adjusts the operation of the battery-powered device based on the identification signal.

3. The system of claim 2, wherein said first performance component configuration enables said industry standard battery pack to support reliable and efficient device operations in accordance with a first mode of operation, and wherein said second performance component configuration enables said customized battery pack to support reliable and efficient device operations in accordance with a second mode of operation.

4. The system of claim 2, wherein said system further comprises:

a sensing device constructed and arranged to detect a presence or absence of said one or more distinguishing features; and a signal generating circuit electrically connected to said sensing device for generating said battery pack performance component configuration identification signal.

5. The system of claim 4, wherein said one or more distinguishing features comprises a recess in said interface of said customized battery pack, wherein said industry standard battery pack does not include a corresponding recess; and wherein said sensing device comprises an electrical switch disposed within the battery pocket constructed and arranged to be activated by said standard interface of said industry standard battery pack and to be received within said recess of said interface of said customized battery pack when said customized battery pack is installed in said battery pocket.

6. The system of claim 5, wherein said switch is a tact switch.

7. The system of claim 5, wherein said switch comprises a spherical actuator, and wherein said recess has a spherical shape adapted to receive said spherical actuator.

8. A battery-powered device having a plurality of modes of operation each having associated therewith a characteristic power source requirement, the device comprising:

a battery pocket constructed and arranged to receive and operate with an industry standard battery pack having a first performance component configuration and standard mechanical and electrical battery interfaces, and a customized battery pack having a second performance component configuration different than said first performance component configuration including a first set of performance components, other than the battery cells, that directly or indirectly affects the ability of the customized battery pack to support the power source requirements dictated by an operational mode of a battery powered device to which the battery pack is connected and a custom interface comprising said standard mechanical battery interface, said standard electrical battery interface and one or more distinguishing features different than said standard battery interface;

a battery performance component configuration identification system constructed and arranged to detect a presence or absence of said one or more distinguishing features and for generating a battery performance component configuration indication signal indicative of said performance components of a battery pack installed in said battery pocket; and a device management system that changes the mode of operation of the battery powered device based on the performance component configuration indication signal.

9. The device of claim 8, wherein the device is a portable defibrillator.

10. The device of claim 8, further comprising:

a device management system for determining said operational mode of said battery-powered device in accordance with said battery performance component configuration indication signal.

11. The device of claim 10, wherein said identification system comprises:

a sensing device constructed and arranged to detect a presence or absence of said one or more distinguishing features; and a controller operationally coupled to said sensing device for generating said battery pack performance component configuration identification signal based on said presence or absence of said one or more distinguishing feature.

12. The device of claim 11, wherein said sensing device comprises an electrical switch disposed within the battery pocket constructed and arranged to be activated by said standard interface of said industry standard battery pack and to be received within a recess of said interface of said customized battery pack when said customized battery pack is installed in said battery pocket.

13. The system of claim 12, wherein said switch is a tact switch.

14. The system of claim 13, wherein said switch comprises a spherical actuator, and wherein said recess has a spherical shape adapted to receive said spherical actuator.

15. The device of claim 10, wherein said distinguishing feature is located on said standard mechanical interface of said customized battery pack.

16. The device of claim 10, wherein said distinguishing feature is located on said standard electrical interface of said customized battery pack.

17. A customized battery pack comprising:

a mechanical interface substantially the same as that provided by a industry standard battery pack;

an electrical interface substantially the same as that provided by said industry standard battery pack;

a first performance component configuration different than a second performance component configuration said industry standard battery pack; and one or more distinguishing features indicative of said first performance component configuration located on one of said mechanical and electrical interfaces, wherein said distinguishing features are not provided on said industry standard battery interface, wherein said performance component includes any operational component implemented in a battery pack, other than battery cells, that affects the ability of a battery pack to support the power source requirements of the device.

18. The system of claim 17, wherein said distinguishing feature comprises a recess in said mechanical interface.

19. The system of claim 18, wherein said recess is spherical in shape.

* * * * *